US012565638B2

(12) United States Patent
Hamazaki et al.

(10) Patent No.: US 12,565,638 B2
(45) Date of Patent: Mar. 3, 2026

(54) METHOD OF DIFFERENTIATING PLURIPOTENT OR EPIBLAST CELLS INTO IMMATURE OOCYTES

(71) Applicant: DIOSEVE INC., Tokyo (JP)

(72) Inventors: Nobuhiko Hamazaki, Tokyo (JP); Katsuhiko Hayashi, Fukuoka (JP)

(73) Assignee: DIOSEVE INC., Tokyo (JP)

( * ) Notice: Subject to any disclaimer, the term of this patent is extended or adjusted under 35 U.S.C. 154(b) by 1000 days.

(21) Appl. No.: 17/642,406

(22) PCT Filed: Sep. 11, 2020

(86) PCT No.: PCT/JP2020/034465
§ 371 (c)(1),
(2) Date: Mar. 11, 2022

(87) PCT Pub. No.: WO2021/049613
PCT Pub. Date: Mar. 18, 2021

(65) Prior Publication Data
US 2022/0333068 A1 Oct. 20, 2022

(30) Foreign Application Priority Data

Sep. 12, 2019 (JP) ................................. 2019-166578

(51) Int. Cl.
| *C12N 5/00* | (2006.01) |
| *C12N 5/0735* | (2010.01) |
| *C12N 5/075* | (2010.01) |
| *C12N 15/85* | (2006.01) |

(52) U.S. Cl.
CPC .......... *C12N 5/0609* (2013.01); *C12N 5/0611* (2013.01); *C12N 15/85* (2013.01); *C12N 2500/90* (2013.01); *C12N 2506/45* (2013.01)

(58) Field of Classification Search
None
See application file for complete search history.

(56) References Cited

U.S. PATENT DOCUMENTS

| | | |
|---|---|---|
| 6,505,434 B1 | 1/2003 | Kloczko et al. |
| 2018/0251729 A1 | 9/2018 | Obata et al. |
| 2020/0362303 A1 | 11/2020 | Saitou et al. |

FOREIGN PATENT DOCUMENTS

| | | | |
|---|---|---|---|
| CN | 102533778 A | | 7/2012 |
| JP | 2002-500864 A | | 1/2002 |
| JP | 2013538038 | * | 10/2013 |
| WO | WO-2017/047799 A1 | | 3/2017 |
| WO | WO-2019/107576 A1 | | 6/2019 |

OTHER PUBLICATIONS

Hayashi (Cell, 2011, vol. 146, No. 4, p. 519-5323).*
Ying, Nature, 2008, vol. 453, No. 7194, p. 519-523.*
Hikabe (Nature 2016, vol. 539, p. 299-303).*
Hu (J. Bioichem., 2012, vol. 113, p. 1111-1121).*
Hu et al., "Characterization of Female Germ-Like Cells Derived From Mouse Embryonic Stem Cells Through expression of GFP Under the Control of Figla Promoter," Journal of Cellular Biochemistry, 2012, 113:1111-1121.
Office Action dated Jun. 18, 2024 in JP 2023-098431, with English machine translation.
Racedo et al. "Effects of Follicle Size and Stages of Maturation on nRNA Expression in Bovine In Vitro Matured Oocytes," Molecular Reproduction and Development, 2008, 75(1):17-25.
Sugawara, Shinchiro, "Mammalian embryo manipulation and its application and future in livestock production (106) XXXIV Genomics of Reproductive Function," Study of Animal Husbandry, 2010, 64(9):925-932.
Yue et al., "Figla Overexpression Induces Differentiation of Mouse Embryonic Stem Cells toward Female Germ Cells," Chinese Journal of Biochemistry and Molecular Biology, 2012, 28(3):240-247, with English abstract.
Gazdag et al., "TBP2 is essential for germ cell development by regulating transcription and chromatin condensation in the oocyte," Genes and Development, Sep. 15, 2009, 23:2210-2223.
Hikabe et al., "Reconstitution in vitro of the entire cycle of the mouse female germ line," Nature, Oct. 17, 2016, 539:299-303.
International Search Report dated Nov. 17, 2020 in PCT/JP2020/034465.
Kristensen et al., "Transcriptional profiling of five isolated size-matched stages of human preantral follicles," Molecular and Cellular Endocrinology, Dec. 17, 2014, 401:189-201.
Murphy et al., "Expression of Stat3 in germ cells of developing and adult mouse ovaries and testes," Gene Expression Patterns, Apr. 2005, 5(4):475-482.
Pangas et al., "oogenesis required germ cell-specific transcriptional regulators Sohlh1 and Lhx8," PNAS, May 23, 2006, 103(21):8090-8095.
Hamazaki et al., "Reconstitution of the oocyte transcriptional network with transcription factors," Nature, Jan. 14, 2021 589(7841):264-269.
Morohaku et al,. "Complete in vitro generation of fertile oocytes from mouse primordial germ cells," Proceedings of the National Academy of Sciences, Jul. 25, 2016, 113(32):9021-9026.
Supplementary European Search Report dated Aug. 25, 2023 in EP 20863911.2.

(Continued)

*Primary Examiner* — Michael C Wilson
(74) *Attorney, Agent, or Firm* — Foley & Lardner LLP

(57) ABSTRACT

A method for inducing immature oocytes includes introducing four genes consisting of FIGLA, NOBOX, LHX8 and TBPL2, or transcripts or expressed proteins thereof, into at least one type of cell selected from the group consisting of pluripotent stem cells, epiblast-like cells and primordial germ cells. A method for producing mature oocytes includes introducing four genes consisting of FIGLA, NOBOX, LHX8 and TBPL2, or transcripts or expressed proteins thereof, into at least one type of cell selected from the group consisting of pluripotent stem cells, epiblast-like cells and primordial germ cells, and co-culturing the cell obtained after the introduction and ovarian somatic cells.

9 Claims, 4 Drawing Sheets

(56) References Cited

OTHER PUBLICATIONS

Office Action dated Jul. 17, 2024 in EP 20863911.2.
Hikabe et al., "Reconstitution in vitro of the entire cycle of the mouse female germ line," Nature, Oct. 17, 2016, 539:299-303, with 12 pages of extended data.
Office Action dated Apr. 23, 2025 in JP 2023-098431, with English translation.

* cited by examiner

FIG. 3

METHOD OF DIFFERENTIATING PLURIPOTENT OR EPIBLAST CELLS INTO IMMATURE OOCYTES

TECHNICAL FIELD

The present invention relates to a method for inducing immature oocytes and a method for producing mature oocytes.

This application is the U.S. National stage of PCT/JP2020/034465, filed Sep. 11, 2020, which claims priority based on Japanese Patent Application No. 2019-166578, which was filed on Sep. 12, 2019 in Japan and the contents of which are incorporated herein.

BACKGROUND ART

In mammals, totipotency defined as the ability of a one cell to develop an organism is an intrinsic property of the single cell. However, elucidation of the mechanism of forming totipotency is facing hard going, although it is in the field that there is a strong social demand such as infertility treatment. This is because the oogenesis process, which progresses in the fetal ovary, cannot be reproduced outside the body.

The inventors have already developed an in vitro culture system for reconstructing oocytes from mouse pluripotent stem cells. Specifically, mouse ES cells or iPS cells are differentiated/induced into primordial germ cell-like cells (PGCLCs) by use of a medium containing a humoral factor, such as BMP4, and the obtained PGCLCs are mixed with ovarian somatic cells to produce reconstructed ovary. The period from PGCLCs until ova in the metaphase of the second meiotic division is formed in the reconstructed ovary, is divided into three periods "in vitro differentiation period", "in vitro growth period" and "in vitro maturation period". In these periods, optimal culture conditions for obtaining secondary ovarian follicles, ova in the germinal vesicle stage and ova in the metaphase of the second meiotic division, respectively, have been established (for example, see, Non-Patent Literature 1).

However, in order to obtain oocytes of the primordial ovarian follicle from mouse pluripotent stem cells by the method described in Non-Patent Literature 1, the period of about 3 weeks or more and 4 weeks or less is required. In primates and other large mammals, it is estimated that the culture period of one or more years is required for producing oocytes from pluripotent stem cells in an in vitro culture system.

CITATION LIST

Non-Patent Literature

Non-Patent Literature 1: Hikabe O, et al., "Reconstitution in vitro of the entire cycle of the mouse female germ line", Nature, Vol. 539, p 299-303, 2016.

SUMMARY OF INVENTION

Technical Problem

The present invention was attained in consideration of the above circumstances and provides a method for inducing immature oocytes from cells having an ability to differentiate into oocytes, such as pluripotent stem cells, easily by culturing for a shorter period than a conventional method.

The present invention also provides a method for producing mature oocytes from cells having an ability to differentiate into oocytes, such as pluripotent stem cells, easily by culturing for a shorter period than a conventional method.

Solution to Problem

The inventors intensively conducted studies with the view to attaining the above objects. As a result, the inventors found that differentiation induction into immature oocytes can be attained by introducing predetermined genes involved in formation of oocytes into pluripotent stem cells and culturing the pluripotent stem cells for a short period of about 5 days or more and 10 days or less. Based on the finding, the present invention was accomplished.

More specifically, the present invention includes the following aspects.

A method for inducing immature oocytes according to a first aspect of the present invention includes introducing four genes consisting of FIGLA, NOBOX, LHX8 and TBPL2, or transcripts or expressed proteins thereof, into at least one type of cell selected from the group consisting of pluripotent stem cells, epiblast-like cells and primordial germ cells.

The method for inducing immature oocytes according to the first aspect may include introducing four genes consisting of FIGLA, NOBOX, LHX8 and TBPL2 into the cell.

The method for inducing immature oocytes according to the first aspect may include further introducing STAT3 gene, or a transcript or expressed protein thereof, into the cell.

The method for inducing immature oocytes according to the first aspect may include further introducing at least one gene selected from the group consisting of SOHLH1, SUB1 and DYNLL1, or a transcript or expressed protein thereof, into the cell.

The method for inducing immature oocytes according to the first aspect may include further introducing three genes consisting of SOHLH1, SUB1 and DYNLL1, into the cell.

The cell may be a pluripotent stem cell.

In the method for inducing immature oocytes according to the first aspect, the expression of the gene is controlled to be induced by the presence of an expression-inducing substance, or the expression of the gene is controlled to be stabilized by the presence of an expression-stabilizing substance, and the method may further include proliferating the cell after the introduction, adding the expression-inducing substance to a culture medium after the proliferation to induce expression of the gene, or adding the expression-stabilizing substance to a culture medium after the proliferation to stabilize expression of the gene.

A method for producing mature oocytes according to a second aspect of the present invention, including introducing four genes consisting of FIGLA, NOBOX, LHX8 and TBPL2, or transcripts or expressed proteins thereof, into at least one type of cell selected from the group consisting of pluripotent stem cells and primordial germ cells, and co-culturing the cell obtained after the introduction and ovarian somatic cells.

The method for producing mature oocytes according to a second aspect of the present invention may include further introducing STAT3 gene or a transcript or expressed protein thereof, into the cell.

Advantageous Effects of Invention

According to the method for inducing immature oocytes of the above aspects, it is possible to induce immature oocytes from cells having an ability to differentiate into oocytes, such as pluripotent stem cells easily by culturing them for a shorter period than a conventional method. According to the method for producing mature oocytes of the above aspects, it is possible to produce mature oocytes from cells having an ability to differentiate into oocytes, such as pluripotent stem cells, easily in a large amount by culturing for a shorter period than a conventional method.

BRIEF DESCRIPTION OF DRAWINGS

FIG. 3 shows a bright-field image and a fluorescent image (magnification: 8×) of immature oocytes induced from mouse iPS cells in Example 2.

DESCRIPTION OF EMBODIMENTS

<Method for Inducing Immature Oocytes>

Figure 1:
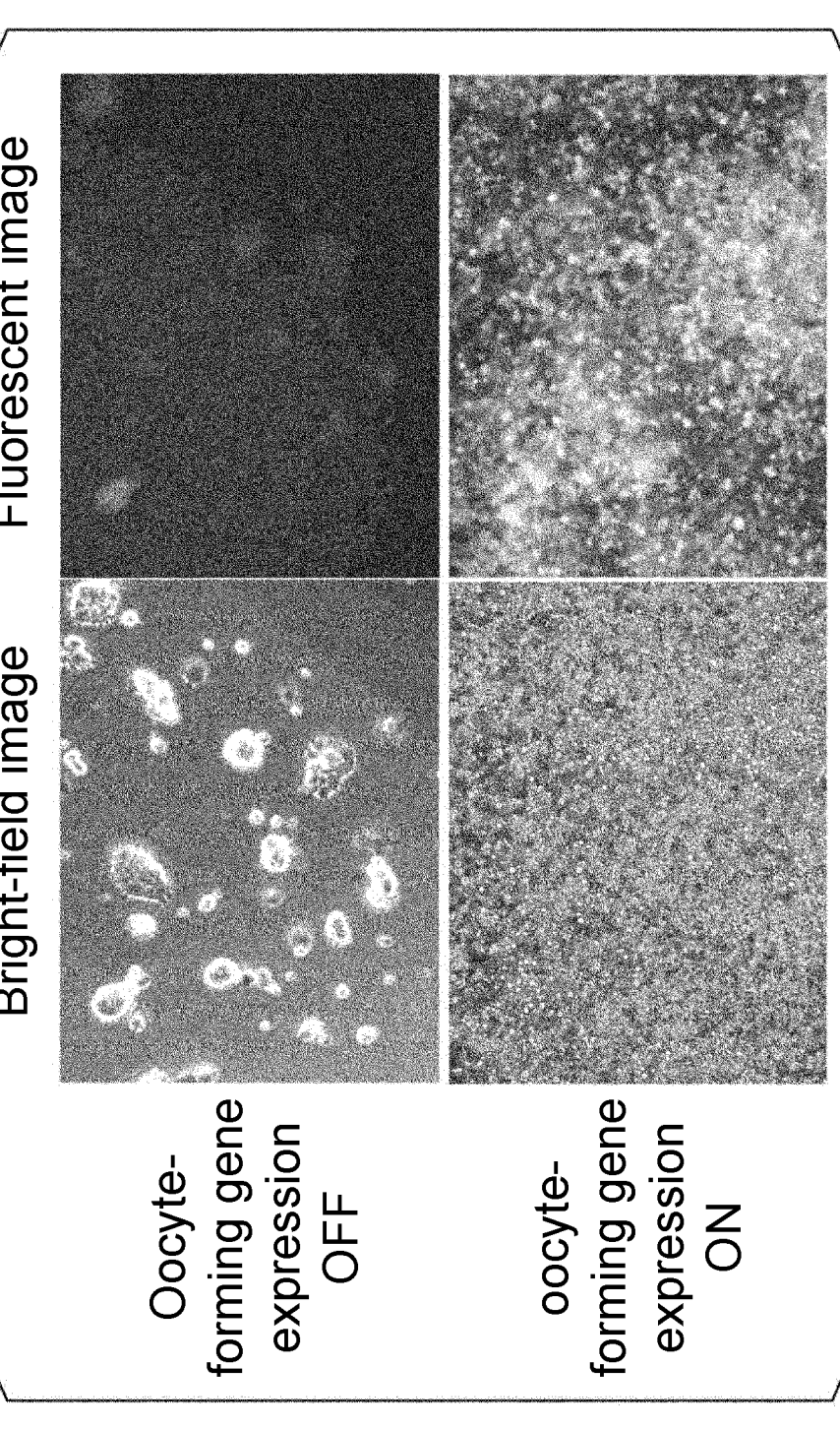
FIG. 1 shows bright-field images and fluorescent images (magnification: 200×) of immature oocytes derived from mouse ES cells in Example 1.

In an embodiment, the present invention provides a method for inducing immature oocytes including introducing four genes consisting of FIGLA, NOBOX, LHX8 and TBPL2, or transcripts or expressed proteins thereof, into at least one type of cell selected from the group consisting of pluripotent stem cells, epiblast-like cells and primordial germ cells (hereinafter sometimes collectively referred to as "cells having an ability to differentiate into oocytes").

In conventional methods, in the case of using mouse, it takes time nearly one month to differentiate/induce pluripotent stem cells into immature oocytes, in vitro, and also, about 11 days to differentiate/induce primordial germ cells into immature oocytes, in vitro. In contrast, in the method for inducing immature oocytes according to the embodiment, immature oocytes can be differentiated/induced by introducing the aforementioned four genes into the cell having an ability to differentiate into oocytes, such as pluripotent stem cells, and culturing them for a short period of about 5 days or more and 10 days or less. Further, in the case of a human, it takes a period of 9 months or more to differentiate/induce immature oocytes from primordial germ cells in vivo; however, the period can be dramatically reduced by use of the method for inducing immature oocytes according to the embodiment.

In conventional methods, at least two steps different in culture conditions are required in order to differentiate/induce pluripotent stem cells into PGCLCs, and then, differentiate/induce the PGCLCs into immature oocytes. In contrast, in the method for inducing immature oocytes according to the embodiment, pluripotent stem cells can be directly differentiated/induced into immature oocytes.

Note that, in the specification, the "immature oocyte" refers to a primary oocyte in which folliculogenesis does not take place. The immature oocyte is not necessary to form an ovarian follicle structure. In the immature oocyte, some of maternal-effect genes, such as Stella gene and Padi6 gene, serving as an oocyte marker, are expressed, as shown in Examples described later.

In the specification, the "ovarian follicle" consists of an oocyte and somatic cells (granulosa cells and capsular cells) surrounding the oocyte.

The method for inducing immature oocytes according to the embodiment will be more specifically described below.

[Oocyte-Forming Genes]

The oocyte-forming genes to be introduced into a cell having an ability to differentiate into an oocyte, such as a pluripotent stem cell, have been already identified by the inventors through RNA sequence (RNA-Seq) analysis of gene expression dynamics in oocyte lineage. Examples of the oocyte-forming gene include FIGLA, NOBOX, SOHLH1, LHX8, SUB1, STAT3, TBPL2 and DYNLL1. Four genes consisting of FIGLA, NOBOX, LHX8 and TBPL2, are particularly important for inducing immature oocytes from pluripotent stem cells, as shown in Examples described later. Of the oocyte-forming genes above, at least four genes consisting of FIGLA, NOBOX, LHX8 and TBPL2, or transcripts or expressed proteins thereof (preferably at least the above-mentioned four genes) are introduced into a cell to induce the cell having an ability to differentiate, to immature oocytes.

In addition to the four genes, or transcripts or expressed proteins thereof, a further introduction of STAT3 gene, or a transcript or expressed protein thereof, is preferable and a further introduction of STAT3 gene is more preferable. As shown in Examples described later, if STAT3 is introduced into cells in addition to FIGLA, NOBOX, LHX8 and TBPL2, the rate of oocyte formation can be enhanced.

In addition to the five genes, FIGLA, NOBOX, LHX8, TBPL2 and STAT3, or transcripts or expressed proteins thereof, one or more gene(S) selected from the group consisting of SOHLH1, SUB1 and DYNLL1, or a transcript or expressed protein thereof is preferably further introduced; and three genes consisting of SOHLH1, SUB1 and DYNLL1, or transcripts or expressed proteins thereof are more preferably further introduced; and three genes consisting of SOHLH1, SUB1 and DYNLL1 are still more preferably further introduced. As shown in Examples described later, if all of the above eight genes, or transcripts or expressed proteins thereof (preferably all of the above eight genes) are introduced into a cell, a cell having an ability to differentiate can be more efficiently induced into an immature oocyte.

Note that, FIGLA gene encodes a basic helix-loop-helix (bHLH) transcription factor, which controls a plurality of oocyte-specific genes (including genes involved in folliculogenesis and genes encoding zona pellucidas (ZP1, ZP2 and ZP3)). Transcription factor FIGLA binds to E-box (5'-CANNTG-3') of ZP (ZP1, ZP2 and ZP3) promoter. Examples of a disease associated with FIGLA include premature ovarian failure (type 6) and pseudo-hermaphroditism. Examples of FIGLA gene ontology (GO) annotation include sequence specific DNA binding ability and protein dimerization activity. An important paralog of FIGLA is SCX. FIGLA is also referred to as a Folliculogenesis Specific BHLH Transcription Factor, Factor In The Germline Alpha, Folliculogenesis-Specific Basic Helix-Loop-Helix Protein, Transcription Factor FIGa, BHLHC8 (BHLHc8), Folliculogenesis Specific Basic Helix-Loop-Helix, FIGALPHA (FIGalpha) or POF6.

Information such as the base sequences of oocyte-forming genes such as FIGLA genes, the base sequences of mRNAs of the genes and amino acid sequences of proteins encoded by the genes, can be obtained from the database of, e.g., Genbank.

The base sequence of human FIGLA gene is disclosed, for example, as "Gene ID: 344018" of the Genbank. The base sequence of mRNA of human FIGLA gene is disclosed, for example, as an accession number of NM_001004311 of the Genbank. The amino acid sequence of human FIGLA is disclosed as an accession number of NP_001004311 of the Genbank.

The base sequence of mouse FIGLA gene is disclosed, for example, as "Gene ID: 26910" of the Genbank. The base sequence of mRNA of mouse FIGLA gene is disclosed, for example, as an accession number of NM_012013 of the Genbank. The amino acid sequence of mouse FIGLA is disclosed as an accession number of NP_036143 of the Genbank.

NOBOX gene encodes a transcription factor involved in oogenesis. Examples of a disease associated with NOBOX include premature ovarian failure (type 5) etc. Examples of NOBOX GO annotation include DNA binding transcription factor activity and DNA binding ability specific to the sequence of a promoter in the vicinity of RNA polymerase II. More specifically, binding is preferably made to a base sequences of, e.g., "5'-TAATTG-3'", "5'-TAGTTG-3'" and "5'-TAATTA-3'." The important paralog of NOBOX is UNCX. NOBOX is also called as NOBOX Oogenesis Homeobox, Homeobox Protein NOBOX, Newborn Ovary Homeobox-Encoding Gene, Newborn Ovary Homeobox-Encoding, TCAG_12042, OG-2(OG2), OG2X or POF5.

The base sequence of human NOBOX gene is disclosed, for example, as "Gene ID: 135935" of the Genbank. The base sequence of mRNA of human NOBOX gene is disclosed, for example, as an accession number of NM_001080413 or XM_001134420 of the Genbank. The amino acid sequence of human NOBOX is disclosed as an accession number of NP_001073882 or XP_001134420 of the Genbank.

The base sequence of mouse NOBOX gene is disclosed, for example, as "Gene ID: 18291" of the Genbank. The base sequence of mRNA of mouse NOBOX gene is disclosed, for example, as an accession number of NM_130869 of the Genbank. The amino acid sequence of mouse NOBOX is disclosed as an accession number of NP_570939 of the Genbank.

SOHLH1 gene is one of gonad specific transcription factors essential for spermatogenesis, oogenesis and folliculogenesis and encodes a basic helix-loop-helix (bHLH) transcription factor. SOHLH1 plays a role in controlling differentiation of oocytes without influencing first meiotic division. Examples of a disease associated with SOHLH1 include non-obstructive azoospermia and gonadal dysplasia. Examples of SOHLH1 GO annotation include DNA binding transcription factor activity and protein dimerization activity. The important paralog of SOHLH1 gene is SOHLH2. SOHLH1 is also referred to as Spermatogenesis And Oogenesis Specific Basic Helix-Loop-Helix 1, Spermatogenesis-And Oogenesis-Specific Basic Helix-Loop-Helix-Containing Protein 1, Spermatogenesis Associated 27, C9orf157, NOHLH, TEB2, Chromosome 9 Open Reading Frame 157, Newborn Ovary Helix Loop Helix, BA100C15.3, SPATA27, BHLHe80, SPGF32 or ODG5.

The base sequence of human SOHLH1 gene is disclosed, for example, as "Gene ID: 402381" of the Genbank. The base sequence of mRNA of human SOHLH1 gene is disclosed, for example, as an accession number of NM_001012415 or XM_497082 of the Genbank. The amino acid sequence of human SOHLH1 is disclosed as an accession number of NP_001012415 or XP_497082 of the Genbank.

The base sequence of mouse SOHLH1 gene is disclosed, for example, as "Gene ID: 227631" of the Genbank. The base sequence of mRNA of mouse SOHLH1 gene is disclosed, for example, as an accession number of NM_001001714 or XM_130180 of the Genbank. The amino acid sequence of mouse SOHLH1 is disclosed as an accession number of NP_001001714 or XP_130180 of the Genbank.

LHX8, which is a protein member of the LIM homeobox family, is involved in pattern formation and differentiation of various tissues. A protein of the LIM homeobox family contains not only DNA-binding homeodomain but also a cysteine-rich double zinc finger motif having two tandem repeats and known as an LIM domain. A protein of the LIM homeobox family is a transcription factor involved in tooth morphogenesis, oogenesis and neuron differentiation. Examples of a disease associated with LHX8 gene include cleft palate and odontoma. LHX8 is also referred to as LIM Homeobox 8, LIM/Homeobox Protein Lhx8, LIM-Homeodomain Protein Lhx8, LIM Homeobox Protein 8 or LHX7.

The base sequence of human LHX8 gene is disclosed, for example, as "Gene ID: 431707" of the Genbank. The base sequence of mRNA of human LHX8 gene is disclosed, for example, as an accession number of NM_001001933, XM_086344, NM_001256114, XM_017001316 or XM_017001317 of the Genbank. The amino acid sequence of human LHX8 is disclosed as an accession number of NP_001001933, XP_086344, NP_001243043, XP_016856805 or XP_016856806 of the Genbank.

The base sequence of mouse LHX8 gene is disclosed, for example, as "Gene ID: 16875" of the Genbank. The base sequence of mRNA of mouse LHX8 gene is disclosed, for example, as an accession number of NM_010713, XM_006501072 or XM_017319470 of the Genbank. The amino acid sequence of mouse LHX8 is disclosed as an accession number of NP_034843, XP_006501135 or XP_017174959 of the Genbank.

SUB1 gene is a gene encoding a transcription modulating factor. SUB1 functions in concert with TAF and serves as a co-activator mediating functional interaction between an upstream activator and general transcription. Examples of a disease associated with SUB1 include nail ringworm etc. Examples of SUB1 GO annotation include single chain DNA binding ability. SUB1 is also referred to as SUB1 Homolog, Transcriptional Regulator, Positive Cofactor 4, Activated RNA Polymerase II Transcriptional Coactivator P15, PC4, P14, Activated RNA Polymerase II Transcription Cofactor 4, RPO2TC1 or P15.

The base sequence of human SUB1 gene is disclosed, for example, as "Gene ID: 10923" of the Genbank. The base sequence of mRNA of human SUB1 gene is disclosed, for example, as an accession number of NM_006713, XM_017008986, XM_017008987 or XM_011513944 of the Genbank. The amino acid sequence of human SUB1 is disclosed as an accession number of NP_006704, XP_016864475, XP_016864476 or XP_011512246 of the Genbank.

The base sequence of mouse SUB1 gene is disclosed, for example, as "Gene ID: 20024" of the Genbank. The base sequence of mRNA of mouse SUB1 gene is disclosed, for example, as an accession number of NM_011294 or XM_006520042 of the Genbank. The amino acid sequence of mouse SUB1 is disclosed as an accession number of NP_035424 or XP_006520105 of the Genbank.

STAT3 is a member of the STAT protein family. The STAT protein family is phosphorylated with a receptor-associated kinase in response to a cytokine and a growth factor such as interferon (IFN), epidermal growth factor (EGF), interleukin 5 (IL5), interleukin 6 (IL6), hepatocyte growth factor (HGF), leukemia inhibitory factor (LIF) and bone morphogenetic protein 2 (BMP2) etc., and then, forms a homo or heterodimer, which migrates into a cell nucleus in which they act as transcriptional activators, and plays an important role in many cellular processes such as cell proliferation and apoptosis. Examples of a disease associated with STAT3 include childhood-onset multi-organ auto-immune disease and autosomal dominant high IgE syndrome etc. Examples of STAT3 GO annotation include DNA binding transcription factor activity and sequence specific DNA binding ability. An important paralog of STAT3 gene is STAT1. STAT3 is also referred to as a Signal Transducer And Activator Of Transcription 3, Acute-Phase Response Factor, APRF, Signal Transducer And Activator Of Transcription 3, DNA-Binding Protein APRF, ADMIO1, ADMIO or HIES.

The base sequence of human STAT3 gene is disclosed, for example, as "Gene ID: 6774" of the Genbank. The base sequence of mRNA of human STAT3 gene is disclosed, for example, as an accession number of NM_001369512, NM_001369513, NM_001369514, NM_001369516, NM_001369517, NM_001369518, NM_001369519, NM_001369520, NM_003150, NM_139276, NM_213662, XM_017024973, XM_011525146, XM_011525145, XM_017024972, XM_005257617, XM_005257616, XM_017024975, XM_024450896, XM_017024974 or XM_017024976 of the Genbank. The amino acid sequence of human STAT3 is disclosed as an accession number of NP_001356441, NP_001356442, NP_001356443, NP_001356445, NP_001356446, NP_001356447, NP_001356448, NP_001356449, NP_003141, NP_644805, NP_998827, XP_016880462, XP_011523448, XP_011523447, XP_016880461, XP_005257674, XP_005257673, XP_016880464, XP_024306664, XP_016880463 or XP_016880465 of the Genbank.

The base sequence of mouse STAT3 gene is disclosed, for example, as "Gene ID: 20848" of the Genbank. The base sequence of mRNA of mouse STAT3 gene is disclosed, for example, as an accession number of NM_011486, NM_213659, NM_213660, XM_011248846 or XM_017314401 of the Genbank. The amino acid sequence of mouse STAT3 is disclosed as an accession number of NP_035616, NP_998824, NP_998825, XP_011247148 or XP_017169890 of the Genbank.

TBPL2 gene is a gene encoding TATA box-binding protein-like 2. TBPL2 is a transcription factor forming a complex with TAF3 in order to induce differentiation of myoblasts into muscle cells. The complex is replaced for TFIID in a predetermined promotor in an initial stage of differentiation. Examples of a disease associated with TBPL2 include retinitis pigmentosa etc. Examples of TBPL2 GO annotation include DNA binding transcription factor activity. An important paralog of TBPL2 gene is TBP. TBPL2 is also referred to as TATA-Box Binding Protein Like 2, TATA Box-Binding Protein-Related Factor 3, TATA Box-Binding Protein-Like Protein 2, TBP-Related Factor 3, TBP-Like Protein 2, TBP2 or TRF3.

The base sequence of human TBPL2 gene is disclosed, for example, as "Gene ID: 387332" of the Genbank. The base sequence of mRNA of human TBPL2 gene is disclosed, for example, as an accession number of NM_199047 of the Genbank. The amino acid sequence of human TBPL2 is disclosed as an accession number of NP_950248 of the Genbank.

The base sequence of mouse TBPL2 gene is disclosed, for example, as "Gene ID: 227606" of the Genbank. The base sequence of mRNA of mouse TBPL2 gene is disclosed, for example, as an accession number of NM_001289689 or NM_199059 of the Genbank. The amino acid sequence of mouse TBPL2 is disclosed as an accession number of NP_001276618 or NP_951014 of the Genbank.

DYNLL1 gene is a gene encoding a protein classified into a light chain of proteins constituting cytoplasmic dynein, which is an enzyme complex having a molecular weight of about 1200 kDa. Examples of a disease associated with DYNLL1 include chronic intestinal venous insufficiency etc. Examples of DYNLL1 GO annotation include protein homodimerization activity and protein domain-specific binding ability. An important paralog of DYNLL1 gene is DYNLL2. DYNLL1 is also referred to as Dynein Light Chain LC8-Type 1, Protein Inhibitor Of Neuronal Nitric Oxide Synthase, Dynein, Cytoplasmic, Light Polypeptide 1, Dynein Light Chain 1, Cytoplasmic, 8 KDa Dynein Light Chain, DNCLC1, DNCL1, DLC1, DLC8, PIN, Cytoplasmic Dynein Light Polypeptide, Hdlc1 (HDLC1), LC8a or LC8.

The base sequence of human DYNLL1 gene is disclosed, for example, as "Gene ID: 8655" of the Genbank. The base sequence of mRNA of human DYNLL1 gene is disclosed, for example, as an accession number of NM_001037494, NM_001037495 or NM_003746 of the Genbank. The amino acid sequence of human DYNLL1 is disclosed as an accession number of NP_001032583, NP_001032584 or NP_003737 of the Genbank.

The base sequence of mouse DYNLL1 gene is disclosed, for example, as "Gene ID: 56455" of the Genbank. The base sequence of mRNA of mouse DYNLL1 gene is disclosed, for example, as an accession number of NM_019682 of the Genbank. The amino acid sequence of mouse DYNLL1 is disclosed as an accession number of NP_062656 of the Genbank.

[Cells Having Ability to Differentiate into Oocytes]

The type of cell having an ability to differentiate into an oocyte to be used in the method for inducing immature oocytes according to the embodiment is preferably at least one selected from the group consisting of pluripotent stem cells, epiblast-like cells (EpiLC) and primordial germ cells.

(Pluripotent Stem Cells)

In the specification, the "pluripotent stem cells" refers to undifferentiated cells having "self-renewal potential", which is an ability to proliferate while keeping an undifferentiated state, and "pluripotency", which is an ability to differentiate into all of the three germ layers. Examples of the pluripotent stem cells include, but are not limited to, for example, induced pluripotent stem cells (iPS cell), embryonic stem cells (ES cell), embryonic germ cells (EG cell) derived from primordial germ cells, multipotent GS (Germline Stem) cells (mGS cell) isolated during the culture process for establishment of GS cells derived from the testes tissue, and Muse cells isolated from bone marrow mesenchymal cells etc.

Note that, ES cells may be those produced from somatic cells by nuclear reprogramming. Individual types of the pluripotent stem cells listed above can be obtained by a known method.

In the specification, the "iPS cells" refers to reprogrammable cells, which are enabled to differentiate into cells of various tissues and organs by introducing some genes into somatic cells already differentiated.

The iPS cells to be used in the method for inducing immature oocytes according to the embodiment may be cells derived from primary culture cells of somatic cells taken from an appropriate donor or derived from an established cell line. Since the iPS cells can be differentiated/induced into any types of germ layer cells, the somatic cells to be used for preparation of iPS cells may be, in principle, those derived from either one of the ectoderm and endoderm cells. Cells such as skin, hair, gingiva and blood, that are less-invasive and easily taken, are preferable as the somatic cells to be used for preparation of iPS cells. The iPS cells may be prepared in accordance with a method known in the technical field, more specifically described, for example, in literatures such as "Okita K. et al., "Generation of germline-competent induced pluripotent stem cells.", Nature, Vol. 448, p 313-317, 2007." (Reference Literature 1), and "Hamanaka S. et al., "Generation of germline-competent rat induced pluripotent stem cells.", PLoS One, Vol. 6, Issue 7, e22008, 2011." (Reference Literature 2).

The ES cells to be used in the method for inducing immature oocytes according to the embodiment can be obtained by a known method. The ES cells can be established, for example, by taking inner cell mass from the blastocyst of a fertilized ovum of a target animal and culturing the inner cell mass on feeder cells derived from fibroblasts. Other than this, ES cells, which are established by culturing the early embryo which is produced by transplanting the nucleus of a somatic cell, can be also used. Further, ES cells can be cultured and maintained in a serum-free medium containing 2i (2 inhibitor; PD0325901 and CHIR99021) and LIF (Leukemia Inhibitory Factor) without using feeder cells, as shown in Examples described later (Reference Literature 3: "Ying Q L et al., "The ground state of embryonic stem cell self-renewal.", Nature, Vol. 453, No. 7194, p 519-523, 2008.").

(Epiblast-Like Cells)

Note that, in the specification, "epiblast-like cells (EpiLC)" are the cells differentiated from pluripotent stem cells (for example, iPS cells, ES cells etc.) in predetermined culture conditions and having analogous properties to those of epiblasts (tissue differentiates in vivo into primordial germ cells).

A method for differentiating/inducing EpiLCs from pluripotent stem cells (iPS cells or ES cells) can be carried out with reference to a known method, described, for example, in Japanese Translation of PCT International Application Publication No. 2013-538038 (Reference Literature 4) and "Hayashi K. et al., "Reconstitution of the mouse germ cell specification pathway in culture by pluripotent stem cells.", Cell, Vol. 146, No. 4, p 519-532, 2011." (Reference Literature 5).

(Primordial Germ Cells)

In the specification, the "primordial germ cells" refers to cells that will be differentiated into germ cells and finally differentiated into ova or sperms through meiosis. The primordial germ cells may be derived from a living body or primordial germ cell-like cells (PGCLC) differentiated/induced from pluripotent stem cells. When primordial germ cells are taken from a living body, primordial germ cells may be collected together with the gonad from, for example, a fetal female mouse (11.5 days old to 12.5 days old). The gonad may be collected from a living body with or without mesonephros.

As described above, examples of the "primordial germ cells" include primordial germ cell-like cells differentiated from pluripotent stem cells. The method for differentiating/inducing PGCLCs from pluripotent stem cells (iPS cells or ES cells) can be carried out in accordance with a known method with reference to, for example, Reference Literature 5 etc.

Note that, when PGCLCs derived from pluripotent stem cells are used as primordial germ cells, it is preferable to remove undifferentiated pluripotent stem cells from a cell population of pluripotent stem cells differentiated/induced, in advance. This kind of method is known in the technical field. If a nucleic acid encoding a fusion protein of Blimp1, which is a marker gene of primordial germ cells, and a reporter protein is previously introduced into, e.g., pluripotent stem cells, PGCLCs differentiated/induced from pluripotent stem cells can be easily separated from undifferentiated cells by, e.g., a fluorescence-activated cell sorting (FACS) method etc.

Examples of the "primordial germ cells" also include cells obtained by modifying the genes of primordial germ cells derived from a living body and primordial germ cell-like cells derived from pluripotent stem cells by use of genetic engineering. Examples of the method for modifying the genes of primordial germ cells derived from a living body and primordial germ cell-like cells derived from pluripotent stem cells include known genome-editing methods such as a method using the CRISPR system and a transcription activator-like effector nucleases (TALEN), a method using a zinc finger nuclease, and a homologous recombination method, by which introduction of desired nucleic acid and vector etc. can be carried out. Examples of the method for introducing a nucleic acid or a vector include a microinjection method, an electroporation method, a lipofection method and nucleic acid introduction method using a viral vector, etc. A method for introducing a foreign gene or a foreign nucleic acid fragment is not limited to those mentioned above as long as primordial germ cells genetically modified can be differentiated into functional oocytes by the method according to the embodiment. Note that, genetic modification for primordial germ cells can be carried out at an appropriate timing during a culture period of the primordial germ cells. For example, it can be carried out in the period from 11.5 days old to 12.5 days old of a mouse. If primordial germ cell-like cells derived from pluripotent stem cells are used, pluripotent stem cells before differentiation induction into primordial germ cell-like cells can be genetically modified by a known method.

As the cells having an ability to differentiate into oocytes to be used in the method for inducing immature oocytes according to the embodiment, pluripotent stem cells are preferable. Of them, if ES cells are used, immature oocytes can be obtained in a large amount since the proliferative ability of the cells is high.

As the cells having an ability to differentiate into oocytes, the cells derived from mammals can be used. Examples of the mammals include, but are not limited to, for example, humans, chimpanzees and other primates; and livestock animals, pet animals and experimental animals etc. such as dog, cat, rabbit, horse, sheep, goat, cow, pig, rat (including nude rat), mouse (including nude mouse and skid mouse), hamster and guinea pig.

[Introduction Step]

In the method for inducing immature oocytes according to the embodiment, the oocyte-forming genes are introduced into at least one type of cell selected from the group consisting of pluripotent stem cells, EpiLCs and primordial germ cells.

In place of an oocyte-forming gene, a transcript mRNA or an expressed protein thereof may be introduced. As the mRNA of an oocyte-forming gene and an expressed protein thereof, mRNA consisting of the base sequence defined by the aforementioned accession number of the Genbank and an expressed protein consisting of the amino acid sequence thereof can be used.

Of these, the above-mentioned oocyte-forming gene is preferably introduced.

The introduction method is not particularly limited and appropriately selected depending on the target cell and the type of substance (e.g., it is a nucleic acid or a protein) to be introduced.

The method for introducing an oocyte-forming gene into a cell is not particularly limited and a method selected from known ones can be appropriately used. Concretely, examples of the method include a lipofection method, a microinjection method, a DEAE dextran method, a gene gun method, an electroporation method and a calcium phosphate method etc.

A method for introducing mRNA of an oocyte-forming gene into cells is not particularly limited and a method selected from known ones can be appropriately used. Examples of the method include a method using a commercially available RNA transfection reagent such as Lipofectamine (registered trademark) MessengerMAX (Life Technologies) etc.

A method for introducing an expressed protein of an oocyte-forming gene into a cell is not particularly limited and a method selected from known ones can be appropriately used. Concretely, examples of the method include a method using an introduction reagent for a protein, a method using a protein transduction domain (PTD) fusion protein and a microinjection method etc.

An oocyte-forming gene may be introduced into at least one type of cell selected from the group consisting of pluripotent stem cells, EpiLCs and primordial germ cells in the form of an expression vector, and may be temporarily expressed therein. Alternatively, an oocyte-forming gene may be integrated into the chromosome of at least one type of cell selected from the group consisting of pluripotent stem cells, EpiLCs and primordial germ cells. Particularly, since a gene can be stably expressed, it is preferable that an oocyte-forming gene is integrated into the chromosome of at least one type of cell selected from the group consisting of pluripotent stem cells, EpiLCs and primordial germ cells.

In the case where an oocyte-forming gene is introduced into at least one type of cell selected from the group consisting of pluripotent stem cells, EpiLCs and primordial germ cells in the form of an expression vector, an expression vector containing the base sequence of the oocyte-forming gene and a promoter thereof controlling the expression of the base sequence of the oocyte-forming gene can be used. In the expression vector, the base sequence of the oocyte-forming gene is functionally ligated to that of the promoter. Of the eight types of oocyte-forming genes, all genes to be used may be integrated in a single expression vector or separately integrated into different types of vectors, one by one. Particularly, in view of introduction efficiency, it is preferable to integrate all genes to be used in a single expression vector.

The promoter, although it is not particularly limited, may be one having an activity in a target cell or an expression inducible promoter whose activity can be induced by a chemical agent etc.

Examples of the promotor having an activity in a target cell include promoters having a strong promoter activity in almost all types of cells, such as a cytomegalovirus promoter (CMV promoter) and CMV early enhancer/chicken beta actin (CAG promoter) etc.

Examples of the expression inducible promoter include a doxycycline-inducible promoter (TetO promoter) etc., the activity of which can be artificially controlled.

The expression vector may contain, if desired, an enhancer, a poly A additional signal, a marker gene, a replication origin, and/or a gene encoding a protein controlling replication by binding to a replication origin, other than the base sequence of an oocyte-forming gene and a promoter. The "marker gene" refers to a gene that enables sorting and selection of cells by introducing said marker gene into cells. Specific examples of the marker gene include a drug resistance gene, a fluorescent protein gene, a gene for a luminescent enzyme and a gene for an enzyme responsible for producing color etc. These marker genes may be used alone or in combination. Specific examples of the drug resistance gene include a puromycin resistance gene, a Geneticin resistance gene, a neomycin resistance gene, a tetracycline resistance gene, a kanamycin resistance gene, a Zeocin resistance gene, a hygromycin resistance gene and a chloramphenicol resistance gene etc. Specific examples of the fluorescent protein gene include a green fluorescent protein (GFP) gene, a yellow fluorescent protein (YFP) gene and a red fluorescent protein (RFP) gene etc. Specific examples of the gene for a luminescent enzyme include a luciferase gene. Specific examples of the gene for an enzyme responsible for producing color include a β-galactosidase gene, a β-glucuronidase gene and an alkaline phosphatase gene etc.

An expression vector to which an oocyte-forming gene is to be integrated is not particularly limited and a known expression vector can be used. Examples of the expression vector include a plasmid vector and a viral vector etc.

The plasmid vector is not particularly limited as long as it can be expressed in at least one type of cell selected from the group consisting of pluripotent stem cells, EpiLCs and primordial germ cells. For example, a plasmid vector commonly used for expressing mammalian cells can be used. Examples of the plasmid vector for expressing mammalian cells include, but are not limited to, for example, pX459, pA1-11, pXT1, pRc/CMV, pRc/RSV and pcDNAI/Neo etc.

Examples of the viral vector include a retrovirus (including lentivirus) vector, an adenovirus vector, an adeno-associated virus vector, a Sendai virus vector, a herpesvirus vector, a vaccinia virus vector, a pox virus vector, a poliovirus vector, a Sindbis virus vector, a rhabdovirus vector, a paramyxovirus vector and an orthomyxovirus vector etc.

Of them, a plasmid vector is preferable as an expression vector.

For integrating an oocyte-forming gene into chromosome, a knock-in system commonly known in the technical field can be used. Examples of the known knock-in system include a method, which includes cleaving chromosome by a known genome-editing method using a CRISPR/Cas system, Transcription Activator-Like Effector Nucleases (TALEN) and a zinc finger nuclease etc., and then, performing homologous recombination by use of a donor vector for homologous recombination, and a method using a transposon vector system.

The donor vector contains base sequences adjacent to a target region, as homology arms. The donor vector may contain the base sequence of an oocyte-forming gene between the 5' arm and the 3' arm (hereinafter sometimes referred to as a "knock-in sequence"). In order to stably express an oocyte-forming gene, it is preferable to set a target region within a safe harbor region.

The donor vector may be a cyclic DNA vector (for example, plasmid vector) or a linear DNA vector. The donor vector may contain other sequences in addition to homology arms and a knock-in sequence. Examples of the other sequences include a marker gene, a replication origin and a gene encoding a protein which binds to a replication origin to control replication. Examples of the marker gene include those mentioned above.

A method for introducing a donor vector, although it is not particularly limited, can be appropriately selected depending on the target cell. Examples of the method for introducing a donor vector into cells include a lipofection method, a microinjection method, a DEAE dextran method, a gene gun method, an electroporation method and a calcium phosphate method etc.

In a transposon vector system, as shown in Examples described later, the transposon vector can be easily integrated into chromosome of a cell by introducing a transposon vector integrating the base sequence of an oocyte-forming gene into the cell and allowing a transposase to act therein. If transposase is again allowed to act, the base sequence of the oocyte-forming gene integrated in the chromosome can be excised out from the chromosome, and the base sequence can be removed without a trace. Examples of the transposon include piggyBac (registered trademark), Hyperactive version of piggyBac (registered trademark) transposase (hyPBase), Sleeping Beauty, Tol II, and mariner etc.

The method for inducing immature oocytes according to the embodiment may include optional steps besides the introduction step. Examples of the optional step include a step of proliferating cells (proliferation step), a step of selecting cells in which an oocyte-forming gene or a transcript or expressed protein thereof is introduced (selection step), and a step of culturing cells after the introduction step under the condition that an oocyte-forming gene is expressed within the cells or an expressed protein of the oocyte-forming gene is present (culture step) etc. If an oocyte-forming gene is introduced in the introduction step, it may include a step of inducing expression of the oocyte-forming gene introduced (expression—introduction step) or a step of stabilizing expression of the oocyte-forming gene introduced (expression stabilization step).

[Proliferation Step]

In the proliferation step, in order to obtain a larger amount of immature oocytes, at least one type of cell selected from the group consisting of pluripotent stem cells, EpiLCs and primordial germ cells, is proliferated.

In the proliferation step, for example, at least one type of cell selected from the group consisting of pluripotent stem cells, EpiLCs and primordial germ cells can be cultured for proliferation in a growth medium. As the growth medium, known mediums used for culturing ES cells, iPS cells, EpiLCs and primordial germ cells etc. can be used but not limited to these, and any culture medium can be used as long as it is suitable for culturing ES cells, iPS cells, EpiLCs and primordial germ cells. More specifically, as the growth medium, e.g., a serum-free medium containing 2i (2 inhibitor; PD0325901 and CHIR99021) and LIF (Leukemia Inhibitory Factor) is mentioned, as shown in Examples described later.

The culture in the proliferation step can be carried out under the conditions known for culturing at least one type of cell selected from the group consisting of pluripotent stem cells, EpiLCs and primordial germ cells. More specifically, for example, the culture temperature can be set at about 30° C. or more and 37° C. or less. Regarding the culture period, although it is not particularly limited in the case of a mouse, it can be set to fall within the range of, for example, about 1 day or more and 10 days or less, about 3 days or more and 7 days or less, or about 5 days. Those skilled in the art can appropriately set a preferable culture period depending on the animal species from which the cells are to be derived.

The proliferation step may be carried out before or after the introduction step. Note that, when the proliferation step is carried out after the introduction step, if an oocyte-forming gene is expressed or a protein expressed by an oocyte-forming gene is present, differentiation induction of at least one type of cell selected from the group consisting of pluripotent stem cells, EpiLCs and primordial germ cells into immature oocytes is initiated. Because of this, proliferation stops. For the reason, as described in the expression induction step/expression stabilization step described later, if the expression of an oocyte-forming gene is controlled to be induced by the presence of an expression-inducing substance, or the expression of an oocyte-forming gene is controlled to be stabilized by the presence of an expression-stabilizing substance, the proliferation step can be carried out under the absence of an expression-inducing substance and expression-stabilizing substance after the introduction step.

When an oocyte-forming gene is introduced in the form of a temporary expression vector or a transcript or expressed protein of an oocyte-forming gene is introduced, the proliferation step is preferably carried out before the introduction step.

[Selection Step]

In the selection step, a cell in which an oocyte-forming gene, a transcript or expressed protein thereof is introduced is selected.

In the selection step, cells introducing an oocyte-forming gene or a transcript or expressed protein thereof can be selected by using, for example, a reporter gene. To describe more specifically, for example, when an oocyte-forming gene is introduced into cells in the form of an expression vector, containing a reporter gene within the expression vector enables selecting cells by expressing reporter gene simultaneously with an oocyte-forming gene expression or independently of the oocyte-forming gene expression, within the cells. When an oocyte-forming gene is integrated into chromosome of at least one type of cell selected from the group consisting of pluripotent stem cells, EpiLCs and primordial germ cells, integrating a construct obtained by ligating a reporter gene functionally to a portion present upstream or downstream of the oocyte-forming gene enables selecting cells by expressing reporter gene simultaneously with an oocyte-forming gene expression or independently of the oocyte-forming gene expression. When a transcript of an oocyte-forming gene is introduced, introducing a construct obtained by ligating the transcript of an reporter gene functionally to a portion present upstream or downstream of the transcript of the oocyte-forming gene in the cells enables selecting cells by expressing the reporter gene simultaneously with an oocyte-forming gene. When expressed protein of an oocyte-forming gene is introduced into cells, introducing a fusion protein of the expressed protein of an oocyte-forming gene and expressed protein of a reporter gene enables selecting cells. As the reporter gene, those illustrated in the above description of the "introduction step" can be used.

[Expression Induction Step/Expression Stabilization Step]

In the introduction step, if the expression of an oocyte-forming gene is controlled to be induced by the presence of an expression-inducing substance, the expression of the oocyte-forming gene is induced by adding the expression-inducing substance in a culture medium. Alternatively, in the introduction step, if the expression of an oocyte-forming gene is controlled to be stabilized by the presence of an expression-stabilizing substance, the expression of the oocyte-forming gene is stabilized by adding the expression-stabilizing substance in a culture medium. In contrast, in the absence of an expression-stabilizing substance, the expressed protein of the oocyte-forming gene expressed is decomposed by proteasome. When immature oocytes are differentiated/induced from at least one type of cell selected from the group consisting of pluripotent stem cells, EpiLCs and primordial germ cells, proliferation of cells stops. For the reason, in order to obtain a larger amount of immature oocytes, it is preferable that a proliferation step is carried out before the expression induction step or expression stabilization step. More specifically, when an oocyte-forming gene is introduced into cells in the form of an expression vector, it is preferable that the proliferation step, the introduction step, and the expression induction step or expression stabilization step are carried out in this order. In contrast, when an oocyte-forming gene is integrated into chromosome of at least one type of cell selected from the group consisting of pluripotent stem cells, EpiLCs and primordial germ cells, it is preferable that the introduction step, the proliferation step, and the expression induction step or expression stabilization step are carried out in this order.

Expression induction of an oocyte-forming gene include, for example, the method for expressing an oocyte-forming gene by introducing oocyte-forming gene in the form of functionally ligating to an expression inducible promoter (for example, doxycycline-inducible promoter (TetO promoter)) into cells and adding an expression-inducing substance (for example, doxycycline) in a culture medium.

Alternatively, expression stabilization of an oocyte-forming gene includes, for example, a method using ProteoTuner (registered trademark) system (manufactured by Clontech Laboratories, Inc.) etc., as shown in Examples described later. More specifically, introducing a construct obtained by functionally ligating a sequence encoding a destabilization domain (DD, 12 kDa) to a portion present upstream or downstream of an oocyte-forming gene into cells results in immediate decomposition of the fusion protein in which the construct is expressed in the absence of an expression-stabilizing substance by proteasome. In contrast, adding a low molecular compound Shield1 (transmembrane low molecular compound, 750 Da), which serves as an expression-stabilizing substance for protecting from decomposition by proteasome, in a culture medium enables expressing an oocyte-forming gene stably and accumulating it within a cell.

The additive amount of an expression-inducing substance or expression-stabilizing substance is not particularly limited as long as the expression level of an oocyte-forming gene is a concentration to be a desired amount. If the expression-inducing substance is, for example, doxycycline, the concentration thereof in the medium can be, e.g., about 1 nM (1 nmol/L) or more and 10 μM (10 μmol/L) or less. If the expression-stabilizing substance is, for example, Shield1, the concentration thereof in the medium can be, e.g., about 10 nM (10 nmol/L) or more and 10 μM (10 μmol/L) or less, can be about 100 nM (100 nmol/L) or more and 5 μM (5 mol/L) or less, can be about 300 nM (300 nmol/L) or more and 3 μM (3 μmol/L) or less, can be about 400 nM (400 nmol/L) or more and 1 μM (1 μmol/L) or less, or can be about 500 nM (500 nmol/L).

As the culture medium to be used in the expression induction step or expression stabilization step, those illustrated as growth mediums in the aforementioned proliferation step, can be used.

[Culture Step]

In the culture step, the cells obtained after the introduction step are cultured under the condition that an oocyte-forming gene is expressed in the cells or an expressed protein of the oocyte-forming gene is present therein.

The culture can be carried out in the known conditions for culturing at least one type of cell selected from the group consisting of pluripotent stem cells, EpiLCs and primordial germ cells. More specifically, for example, the culture temperature can be set at about 30° C. or more and 37° C. or less. The culture period, in the case of a mouse, can be set to fall within the range of, for example, about 1 day or more and 10 days or less, or about 3 days or more and 7 days or less.

As a culture medium to be used in the culture step, those illustrated as the growth mediums in the proliferation step can be used. Note that, if the expression of an oocyte-forming gene is controlled to be induced by the presence of an expression-inducing substance, the cells are cultured under the condition of that the above-mentioned expression-inducing substance is added to the culture medium and the oocyte-forming gene is expressed in the cell. Alternatively, if the expression of an oocyte-forming gene is controlled to be stabilized by the presence of an expression-stabilizing substance, the cells are cultured under the condition of that expression-stabilizing substance is added to the culture medium and the oocyte-forming gene is expressed in the cell.

In a method for inducing immature oocytes according to a preferable embodiment, the expression of an oocyte-forming gene is controlled to be induced by the presence of an expression-inducing substance, or the expression of an oocyte-forming gene is controlled to be stabilized by the presence of an expression-stabilizing substance, and the method includes the following 1) to 5):

1) introducing four oocyte-forming genes of FIGLA, NOBOX, LHX8, and TBPL2 (preferably five types of oocyte-forming genes of FIGLA, NOBOX, LHX8, TBPL2, and STAT3; and more preferably, eight types of oocyte-forming genes of FIGLA, NOBOX, LHX8, TBPL2, STAT3, SOHLH1, SUB1, and DYNLL1) into chromosome of at least one type of cell selected from the group consisting of pluripotent stem cells, EpiLCs and primordial germ cells (particularly preferably, a pluripotent stem cell);

2) proliferating the cells obtained after the introduction;

3) selecting cells in which the oocyte-forming genes are introduced in the chromosome from the cells obtained after the proliferation;

4) inducing expression of the oocyte-forming genes by adding an expression-inducing substance in the culture medium in the cells obtained after the selection or stabilizing the expression of an oocyte-forming genes by adding an expression-stabilizing substance in the culture medium in the cells obtained after the selection; and 5) culturing the cells obtained after inducing the expression or after stabilizing the expression, in the state where the oocyte-forming genes are expressed in the cells.

In a method for inducing immature oocytes according to a more preferable embodiment, the expression of an oocyte-forming gene is controlled by the ProteoTuner (registered trademark) system. The method includes the following 1) to 5).

1) introducing a construct obtained by functionally ligating a sequence encoding a destabilization domain (DD, 12 kDa) to a portion present upstream or downstream of four oocyte-forming genes of FIGLA, NOBOX, LHX8, and TBPL2 (preferably five types of oocyte-forming genes of FIGLA, NOBOX, LHX8, TBPL2, and STAT3; and more preferably, eight types of oocyte-forming genes, FIGLA, NOBOX, LHX8, TBPL2, STAT3, SOHLH1, SUB1, and DYNLL1) into chromosome of pluripotent stem cells;

2) proliferating the cells obtained after the introduction;

3) selecting cells in which the oocyte-forming genes are introduced in the chromosome from the cells obtained after the proliferation;

4) stabilizing expression of the oocyte-forming genes in the cells obtained after the selection by adding Shield1 in the culture medium;

5) culturing the cells obtained after the stabilization, in the state where the oocyte-forming genes are expressed in the cells.

In the method for inducing immature oocytes according to the embodiment, as described above, at least one type of cell selected from the group consisting of pluripotent stem cells, EpiLCs and primordial germ cells can be differentiated/induced into immature oocytes in a short culture period of about 5 days or more and 10 days or less from introduction of an oocyte-forming genes or transcripts or expressed proteins thereof.

Differentiation induction of at least one type of cell selected from the group consisting of pluripotent stem cells, EpiLCs and primordial germ cells into immature oocytes can be confirmed based on expression of a known marker gene of oocytes (for example, Stella). More specifically, differentiation induction into immature oocytes can be confirmed by introducing a nucleic acid encoding a fusion protein of Stella and a reporter protein (for example, enhanced cyan fluorescent protein (ECFP)), which is oocyte's marker gene, into chromosome of at least one type of cell selected from the group consisting of pluripotent stem cells, EpiLCs and primordial germ cells, in advance, from fluorescence emitted by expression of Stella-ECFP, as shown in Examples described later. Furthermore, based on expression of Stella-ECFP and in accordance with, e.g., the fluorescence-activated cell sorting (FACS) method, undifferentiated cells can be removed from the cell population obtained after the differentiation induction, with the result that immature oocytes can be easily separated.

<Method for Producing Mature Oocytes>

In an embodiment, the present invention provides, a method for producing mature oocytes, including introducing four genes consisting of FIGLA, NOBOX, LHX8 and TBPL2, or transcripts or expressed proteins thereof, into at least one type of cell selected from the group consisting of pluripotent stem cells, EpiLCs and primordial germ cells, and co-culturing the cell obtained after the introduction and ovarian somatic cells.

In the method for producing mature oocytes of the embodiment, a step of introducing (introduction step) oocyte-forming genes is the same as the introduction step defined in the aforementioned "method for inducing immature oocytes". Thus, explanation thereof is omitted.

Note that, in the specification, the "mature oocyte" refers to an ovum during the metaphase of the second meiotic division and is also called as a secondary oocyte. In the mature oocyte, a marker for an activated oocyte, Npm2 gene, is expressed, as shown in Examples described later.

[Aggregate Forming Step]

The method for producing mature oocytes according to the embodiment includes a step (aggregate forming step) of forming aggregates by co-culturing at least one type of cell selected from the group consisting of pluripotent stem cells, EpiLCs and primordial germ cells which are those after the introduction step described in the above-mentioned "method for inducing oocytes" and ovarian somatic cells.

The ovarian somatic cells to be used in the aggregate forming step are somatic cells taken from the ovary of a living body and differentiate into granulosa cells or capsular cells constituting ovarian follicle if they are co-cultured with at least one type of cell selected from the group consisting of the above-mentioned pluripotent stem cells, EpiLCs and primordial germ cells.

Note that, a method for collecting somatic cells from the ovary of a living body can be carried out as illustrated in the description of Reference Literature 5.

More specifically, in the method for collecting somatic cells from the ovary, somatic cells constituting the ovary can be dissociated by that the ovary is surgically taken from a living body, and treated with trypsin etc. Note that, it is preferable herein to remove germ cells present within the ovary derived from a living body. The method for removing germ cells present within the ovary can be carried out in accordance with a known method, and for example, germ cells present within the ovary can be removed by a magnetic activated cell sorting method using an anti-SSEA1 antibody and an anti-CD31 antibody. Herein, the ovary from which ovarian somatic cells are collected is preferably derived from a fetus. In the case of a mouse, the gonad (ovary) derived from a mouse fetus of 12.5 days old in terms of fetus age (also referred to as "embryo age") can be used. Those skilled in the art can appropriately select the gonad (ovary) of a preferable age depending on the animal species from which the ovarian somatic cells are to be derived, based on disclosure of the invention and the common knowledge in the technical field.

In the aggregate forming step, it is preferable that at least one type of cell selected from the group consisting of pluripotent stem cells, EpiLCs and primordial germ cells which are obtained after the introduction step and ovarian somatic cells are co-cultured to form aggregates of them constituted of the at least one type of cell selected from the group consisting of pluripotent stem cells, EpiLCs and primordial germ cells which are obtained after the introduction step and the ovarian somatic cells.

A method for producing aggregates consisting of at least one type of cell selected from the group consisting of pluripotent stem cells, EpiLCs and primordial germ cells after the introduction step, and ovarian somatic cells can be carried out by mixing at least one type of cell selected from the group consisting of pluripotent stem cells, EpiLCs and primordial germ cells obtained after the introduction step and ovarian somatic cells in S10 culture medium (StemPro (registered trademark)-34 SFM, manufactured by Life Technologies Corporation) containing 10% fetal bovine serum (FCS), 150 μM ascorbic acid, 1× GlutaMax, 1× penicillin/streptomycin and 55 μM mercaptoethanol, aggregating and culturing the cells, for example, as shown in Examples described later. Note that, in the case where the expression of an oocyte-forming gene is controlled to be induced by the presence of an expression-inducing substance, or the expression of an oocyte-forming gene is controlled to be stabilized by the presence of an expression-stabilizing substance, culture is carried out in the state where an oocyte-forming gene is expressed by addition of the above expression-inducing substance or the above expression-stabilizing substance to a culture medium. For culturing, a low-adsorption culture dish (for example, a low cell-adhesive 96-well plate with U-bottom) is preferably used.

In the case of a mouse, for example, the culture period for preparing aggregates can be set to fall within the range of about 2 days or more and 3 days or less, and preferably 2 days. Those skilled in the art can determine a preferable culture period depending on the animal species from which they are to be derived.

The mixing ratio of at least one type of cell selected from the group consisting of pluripotent stem cells, EpiLCs and primordial germ cells obtained after the introduction step and ovarian somatic cells is not limited as long as aggregates produced of them form mature ovarian follicles. For example, in the case of a mouse, the cell-number ratio of at least one type of cell selected from the group consisting of pluripotent stem cells, EpiLCs and primordial germ cells obtained after the introduction step and ovarian somatic cells is preferably set at about 2:1.

Further, the at least one type of cell selected from the group consisting of pluripotent stem cells, EpiLCs and primordial germ cells obtained after the introduction step, ovarian somatic cells or the ovary containing ovarian somatic cells can be used as cryopreserved cells or ovary. Cryopreservation can be carried out in accordance with a known method. For example, the cells of at least one type of cell selected from the group consisting of pluripotent stem cells, EpiLCs and primordial germ cells obtained after the introduction step and ovarian somatic cells can be cryopreserved in accordance with, e.g., a slow freezing method using a 10% DMSO solution or a commercially available freezing agent (e.g., CELLBANKER (registered trademark)).

Note that, the ovarian somatic cells to be used in the method for producing mature oocytes according to the embodiment may be derived from the same mammalian species as at least one type of cell selected from the group consisting of pluripotent stem cells, EpiLCs and primordial germ cells constituting aggregates or may be derived from a different mammalian species. Preferably, ovarian somatic cells derived from the same mammalian species are used. The mammals include the same as illustrated in the description of the cells having an ability to differentiate into the oocytes.

The method for producing mature oocytes according to the embodiment includes an optional step after the above-mentioned introduction step and before the aggregate forming step. Examples of the optional step include the proliferation step and the selection step, which are illustrated in the description of the "method for inducing immature oocytes" etc. mentioned above.

[Culture Step]

The method for producing mature oocytes according to the embodiment may include a culture step after the above aggregate forming step.

In the culture step, it is preferable that aggregates obtained after the aggregate forming step are transferred onto the collagen membrane and cultured thereon.

Aggregates can be cultured in known culture conditions for culturing aggregates. More specifically, for example, the culture temperature can be set at about 30° C. or more and 37° C. or less. The culture period in the case of a mouse can be set to fall within the range of about 7 days or more and 35 days or less, or about 8 days or more and 30 days or less. Those skilled in the art can appropriately determine a preferable culture period depending on the animal species from which they are to be derived.

As a culture medium to be used in the culture step those illustrated as the growth medium in the aforementioned proliferation step can be used. Note that, in the case that the expression of an oocyte-forming gene is controlled to be induced by the presence of an expression-inducing substance, or the expression of an oocyte-forming gene is controlled to be stabilized by the presence of an expression-stabilizing substance, culture is carried out under the state that an oocyte-forming gene is expressed within cells by addition of the above expression-inducing substance or the above expression-stabilizing substance to a culture medium.

After the culture step, the aggregates have a secondary ovarian follicle structure where oocytes are surrounded by multi-layered granulosa cells, and further ovarian follicle membrane (theca folic) which surrounds the multi-layered granulosa cells is formed. The theca cells constituting the theca interna express a luteinizing hormone receptor, and granulosa cells express an ovarian follicle stimulating hormone receptor.

Subsequently, ovarian follicles obtained in the culture step are cultured in accordance with the method described in Non-Patent Literature 1 to produce mature oocytes. More specifically, the step until mature oocytes are obtained is divided into a growth step and a maturation step.

[Growth Step]

In the growth step, ovarian follicles obtained in the culture step are separated into discrete ovarian follicles and cultured in a growth medium.

Culture can be carried out under the conditions described in Non-Patent Literature 1. More specifically, for example, the culture temperature can be set at about 30° C. or more and 37° C. or less. The culture period in the case of a mouse can be set to fall within the range of about 7 days or more and 15 days or less, or about 8 days or more and 13 days or less. Those skilled in the art can appropriately set a preferable culture period depending on the animal species from which the ovarian follicle is to be derived.

As a growth medium, a medium having a composition described in Non-Patent Literature 1 can be used. More specifically, for example, in the case of a mouse, an ovarian follicle is cultured in α-MEM containing 5% fetal bovine serum (FCS), 2% polyvinylpyrrolidone (these are all manufactured by Sigma Corporation), 150 μM ascorbic acid, 1× GlutaMAX, 1× penicillin/streptomycin, 100 μM 2-mercaptoethanol, 55 μg/mL sodium pyruvate (these are all manufactured by Nacalai Tesque Inc.), 0.1 IU/mL ovarian follicle stimulating hormone (Follistim (registered trademark), manufactured by MSD K.K.), 15 ng/mL BMP15 (bone morphogenetic protein 15), and 15 ng/mL GDF9 (growth differentiation factor 9) (these are all manufactured by R&D Systems, Inc.), for two days from initiation of culture. At Day 2 after initiation of the culture, the medium is exchanged with α-MEM containing the above components except BMP15 and GDF9 and the ovarian follicle is cultured in 0.1% TypeIV collagenase (manufactured by MP Biomedicals). Subsequently, washing is carried out several times with 5% FCS containing α-MEM and then the ovarian follicle is cultured in α-MEM containing the above components except BMP15 and GDF9, up to Day 11 after initiation of the culture.

The ovarian follicle obtained after the growth step has a vesicular follicle structure and forms a cumulus-oocyte complex having an ovum of a germinal vesicle stage.

[Maturation Step]

In the maturation step, the ovarian follicle obtained in the growth step is cultured in a medium for maturation.

Culture can be carried out under the conditions described in Non Patent Literature 1. More specifically, for example, the culture temperature can be set at about 30° C. or more and 37° C. or less. The culture period in the case of a mouse can be set to fall within the range of about 7 days or more and 15 days or less, or about 8 days or more and 13 days or less. Those skilled in the art can appropriately set a preferable culture period depending on the animal species from which the ovarian follicle is to be derived.

As the medium for maturation, a medium having a composition described in Non-Patent Literature 1 can be used. Examples of the medium in the case of a mouse include α-MEM containing 5% FCS, 25 μg/mL sodium pyruvate, 1× penicillin/streptomycin, 0.1 IU/mL ovarian follicle stimulating hormone, 4 ng EGF (Epidermal Growth Factor) and 1.2 IU/mL hCG (human chorionic gonadotropin, simply referred to as gonadotropin, manufactured by ASKA).

The ovarian follicle obtained after the maturation step is matured up to an ovum (secondary oocyte) in the metaphase of the second meiotic division.

It can be evaluated that it is an ovum (secondary oocyte) in the metaphase of second meiotic division, based on the visual observation of release of a first polar body by a microscope etc.

The resulting mature oocytes (secondary oocyte) are suitably used for infertility treatment. More specifically, according to an embodiment of the present invention, the present invention provides an infertility treatment method using mature oocytes obtained by the above method.

The mature oocytes obtained by the method for producing mature oocytes according to the embodiment are suitably used for efficient breeding of industrial animals and propagation of rare animals. More specifically, according to an embodiment of the present invention, the present invention provides a method for breeding industrial animals or a method for propagating rare animals using mature oocytes obtained by the above method.

Note that, the animals to which the method is to be applied are preferably mammals. Examples of the mammals include the same as those mentioned above.

The mature oocytes obtained by the method for producing mature oocytes according to the embodiment are useful for finding a cause of infertility and elucidating mechanism of menopausal diseases.

EXAMPLES

Now, the present invention will be more specifically described by way of Examples but the present invention is not limited by the following Examples.

Example 1

(Construction of Vector)

A CAG promoter and a destabilization domain (DD) were cloned from CAG-DD-hTFAP2C plasmid (Reference Literature 6: "Kobayashi T et al., "Principles of early human development and germ cell program from conserved model systems.", Nature, Vol. 546, No. 7658, p 416-420, 2017.") and inserted into PiggyBAC vector routinely used (Reference Literature 7: "Shimamoto S et al., "Hypoxia induces the dormant state in oocytes through expression of Foxo3", PNAS, https:////doi.org/10.1073/pnas.1817223116, 2019.") to produce PB-CAG-DD vector. Then, cDNA of eight genes, FIGLA, NOBOX, SOHLH1, LHX8, SUB1, STAT3, TBPL2 and DYNLL1, were amplified from cDNA of the ovary of a female mouse of 13.5 days after fertilization and cloned to a PB-CAG-DD vector by use of an infusion HD cloning kit (manufactured by Takara Bio Inc.). Individual cDNA molecules were amplified by PCR using KOD Fx Neo or KOD Plus Neo DNA polymerase (manufactured by TOYOBO Co. Ltd.) in accordance with the manufacturer's protocol.

(Transfection by Vector)

ES cells were previously cultured and maintained in a serum-free medium containing 2i and LIF without using feeder cells (see, Reference Literature 3). In order to monitor differentiation into immature oocytes and mature oocytes, mouse ES cells (Blimp1-mVenus:Stella-ECFP:Npm2-mCherry (BVSCNmC)) were used, which have a gene encoding mVenus (membrane-targeted Venus), which is variant of yellow fluorescent protein (YFP) whose expression is controlled by Blimp1, which is an important determinant of a germline; a gene encoding an enhanced cyan fluorescent protein (ECFP) which is modified under controlling the expression of Stella, which is a germ cell and oocyte marker; and a gene encoding a red fluorescent protein mCherry (membrane-targeted Cherry) which is under controlling the expression of Nucleoplasmin 2 (Npm2), which is a marker for activated (maturity) oocytes, inserted into the chromosome thereof. The constructed PB-CAG-DD vector containing eight genes was transfected simultaneously with hyperactive PBase (hypBase) plasmid by Lipofectamine 2000. After proliferation was carried out by performing culture in a serum-free medium containing 2i and LIF at 37° C. for 5 days, a single colony was obtained by puromycin selection.

(Differentiation Induction into Immature Oocyte)

Subsequently, $1\times10^5$ ES cells obtained after puromycin selection were transferred to a low cell-adhesive 96-well plate with U-bottom, into which culture medium that 0.5 μM Shield1 (manufactured by Clontech Laboratories, Inc.) was mixed to S10 culture medium (StemPro (registered trademark)-34 SFM, manufactured by Life Technologies Corporation) containing 10% fetal bovine serum (FCS), 150 μM ascorbic acid, 1× GlutaMax, 1× penicillin/streptomycin and 55 μM mercaptoethanol (hereinafter referred to as "oocyte differentiation induction medium") was dispense, and then, cultured at 37° C. for 5 days to differentiate/induce into immature oocytes. The results of observation under a confocal microscope (model number: Zeiss LSM 700, manufactured by Carl Zeiss) are shown in FIG. 1. In FIG. 1, "oocyte-forming genes" refer to eight genes of FIGLA, NOBOX, SOHLH1, LHX8, SUB1, STAT3, TBPL2 and DYNLL1. The "oocyte-forming gene expression OFF" refers to cells before adding a medium containing Shield1, whereas the "oocyte-forming gene expression ON" refers to cells after having cultured in a medium containing Shield1 for 5 days.

From FIG. 1, it was found that the cells of which oocyte-forming gene expression is OFF form colonies and that fluorescence of ECFP (Stella-ECFP) emitted under expression control by Stella is rarely observed. In contrast, it was found that the cells of which the oocyte-forming gene expression is ON are discretely present one another and that strong fluorescence from Stella-ECFP is detected, and it was suggested that ES cells are differentiated/induced into immature oocytes.

(Preparation of Mature Oocyte)

Figure 2:
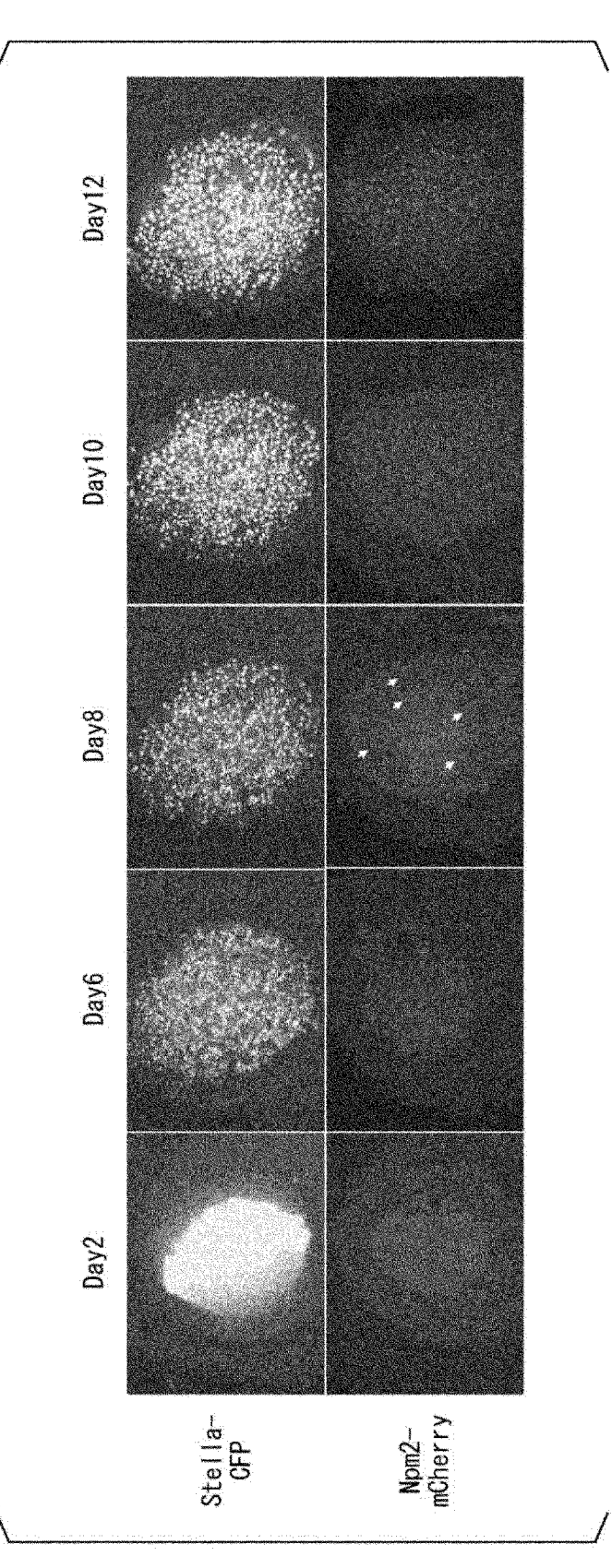
FIG. 2 shows fluorescent images (magnification: 8×) of aggregates, which consist of pluripotent stem cells having oocyte-forming genes are introduced and ovarian somatic cells, according to Example 1 at individual culture days. The upper column shows fluorescent images of the oocytes visualized by an enhanced cyan fluorescent protein (ECFP) expressed under control of Stella serving as a marker for germ cells and oocytes. The lower column shows fluorescent images of the oocytes visualized by a red fluorescent protein mCherry expressed under control by Nucleoplasmin 2 (Npm2) serving as a marker for activated (mature) oocytes.

Subsequently, after transfection in the above section (transfection by vector), single colony of ES cells (1×10⁵ cells), which were proliferated by culturing at 37° C. for 5 days and then selected by puromycin, were mixed with ovarian somatic cells (3×10⁴ cells) derived from a female mouse of 12.5 days old after fertilization to produce aggregates, which were then cultured in the aforementioned oocyte differentiation induction medium at 37° C. for 2 days. Ovarian somatic cells used herein were previously prepared by excising out the ovary from a female mouse of 12.5 days after fertilization and isolating from the ovary in accordance with the method described in, e.g., Non-Patent Literature 1. Subsequently, the aggregates were transferred onto a Transwell-COL membrane (manufactured by Coaster Incorporated) and cultured in the oocyte differentiation induction medium for 28 days. The result of observing the expression of individual markers of aggregates on Day 2, 6, 8, 10 and 12 after initiation of the culture under a confocal microscope (model number: Zeiss LSM 700, manufactured by Carl Zeiss) are shown in FIG. 2. In the upper column of FIG. 2, oocytes are visualized by fluorescence of Stella-ECFP, which serves a marker for germ cells and oocytes. In the lower column, oocytes are visualized by fluorescence of red fluorescent protein mCherry (Npm2-mCherry), which is expressed under control by Nucleoplasmin 2 (Npm2) serving as a marker for activated (mature) oocytes.

From FIG. 2, fluorescence of Stella-ECFP was continuously observed in the cells throughout the culture period. In contrast, fluorescence of Npm2-mCherry was observed on Day 8 from initiation of the culture (see arrows in FIG. 2, "Day 8" in the lower column), suggesting that maturation of the oocytes proceeds.

Day 28 from initiation of the culture, individual ovarian follicles were mutually separated manually with a sharpened tungsten needle. The ovarian follicles separated had a secondary ovarian follicle structure. The ovarian follicle was cultured in culture conditions according to "in vitro growth period" and "in vitro maturation period" described in Non-Patent Literature 1 to mature the ovarian follicle into an ovum in the metaphase of the second meiotic division via vesicular ovarian follicle.

Example 2

Differentiation induction of mouse iPS cells into oocytes was examined in the same manner as ES cells.

(Transfection by Vector)

As the iPS cells, mouse BVSC iPS cells were used, which were prepared by a virus buster established as described in the paper of Non-Patent Literature 1. The PB-CAG-DD vector containing eight genes constructed in Example 1 was transfected into mouse BVSC iPS cells simultaneously with hyperactive PBase (hypBase) plasmid by Lipofectamine 2000. After proliferation was carried out by performing culture in a serum-free medium containing 2i and LIF at 37° C. for 5 days, a single colony was obtained by puromycin selection.

(Differentiation Induction into Immature Oocyte)

After puromycin selection, iPS cells were differentiated/induced into immature oocytes by culturing them at 37° C. for 5 days in the same manner as in Example 1.

(Production of Mature Oocyte)

Figure 3:
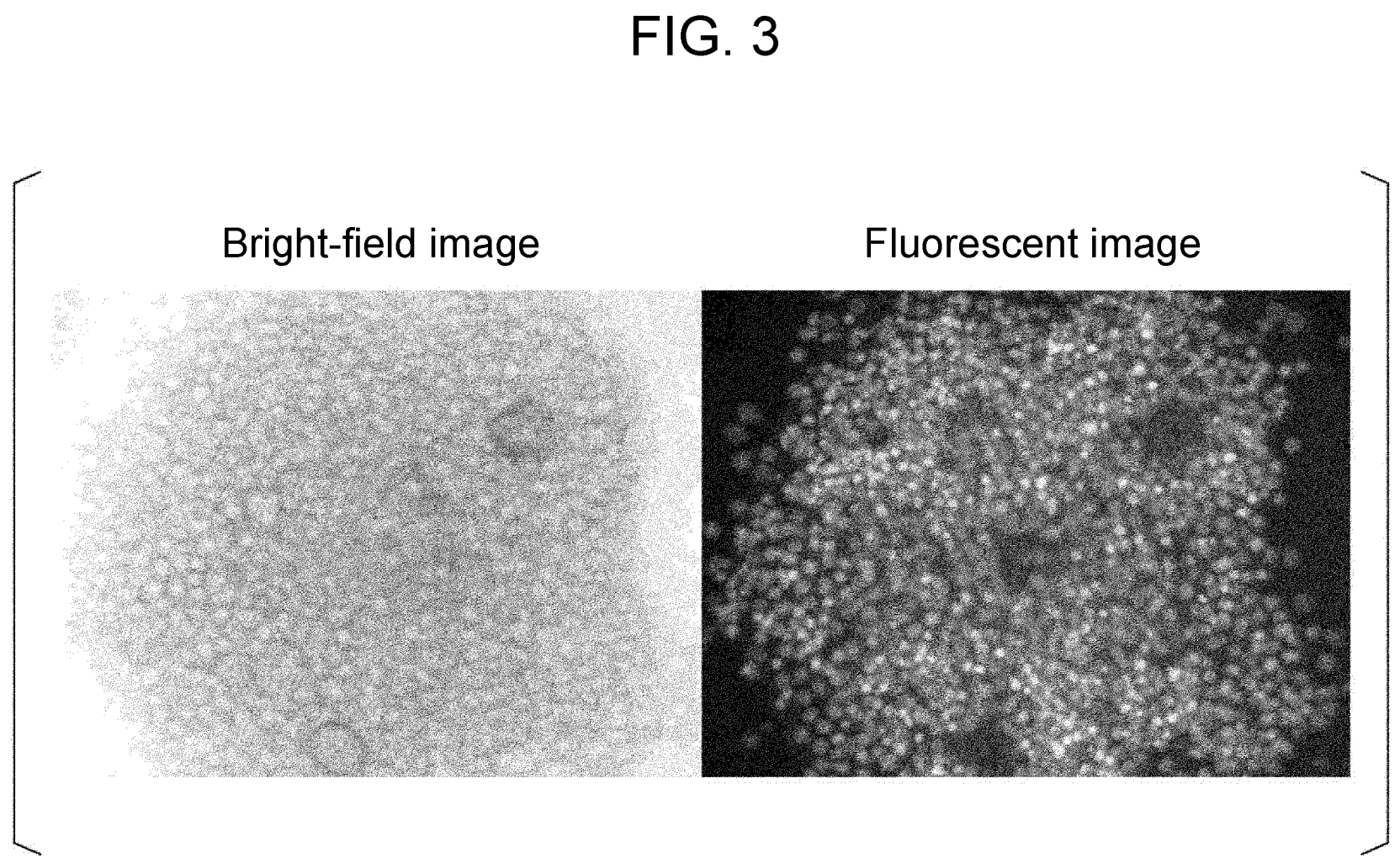

A single colony of iPS cells (1×10⁵ cells), which were proliferated by culturing at 37° C. for 5 days after transfection in the above section "Transfection by vector" and then selected by puromycin, was mixed with ovarian somatic cells (3×10⁴ cells) derived from a female mouse of 12.5 days old after fertilization to produce aggregates, which were then cultured in the aforementioned oocyte differentiation induction medium at 37° C. for 2 days. Subsequently, the aggregates were transferred to a Transwell-COL membrane (manufactured by CoasterIncorporated) and cultured in the oocyte differentiation induction medium for 21 days. The result of observing the expression of Stella-ECFP in aggregates on Day 21 after initiation of the culture under a confocal microscope (model number: Zeiss LSM 700, manufactured by Carl Zeiss) is shown in FIG. 3. In FIG. 3, the image on the left side is a bright-field image and the image on the right side is a fluorescent image of oocytes visualized by fluorescence of Stella-ECFP germ cell and oocyte marker.

From FIG. 3, it was found that Stella-ECFP fluorescence was observed in the cells on Day 21 from initiation of the culture. From the fact, it was confirmed that iPS cells were successfully differentiated/induced into oocytes similarly to ES cells.

Example 3

(Identification of Important Factor in Oocyte-Forming Gene)

Figure 4:
FIG. 4 shows the identification results of important factors in oocyte-forming genes in Example 3. In the left-side table, sample names are shown along the vertical line and types of oocyte-forming genes are shown along the horizontal line. An open column represents that the gene indicated below is not introduced. The center table shows the number of oocytes formed from individual cell strains. The right-side table shows the areas of oocytes calculated based on the fluorescent areas of blue fluorescent protein CFP expressed downstream of Stella gene in individual samples.

In order to identify a gene which is an important factor among the oocyte-forming genes, 26 types of vectors in total were constructed in the same manner as in Example 1 so that the combinations of genes shown in the left-side table of FIG. 4 were obtained. Subsequently, using the same method as in Example 1, the individual vectors were transfected into mouse ES cells (Blimp1-mVenus:Stella-ECFP:Npm2-mCherry (BVSCNmC)). After transfection, single cell-derived ES cells (1×10⁵ cells) which were proliferated by culturing at 37° C. for 5 days and then selected by puromycin, were mixed with ovarian somatic cells (3×10⁴ cells) derived from a female mouse of 12.5 days old after fertilization in the aforementioned oocyte differentiation induction medium to produce aggregates, which were then cultured at 37° C. for 2 days. Subsequently, the aggregates obtained were cultured for 21 days in the same manner as in Example 1. For the cells cultured, the number of oocytes formed from each cell strain was counted. Further, the area of oocytes was calculated based on the fluorescent area of blue fluorescent protein CFP expressed downstream of Stella gene. These results are shown in FIG. 4.

From FIG. 4, it was found that among the oocyte-forming genes, four genes consisting of FIGLA, NOBOX, LHX8 and TBPL2 are important factors for differentiation induction of pluripotent stem cells into immature oocytes and maturation of oocytes. It was also found that when STAT3 gene is introduced in addition to four genes consisting of FIGLA, NOBOX, LHX8 and TBPL2, the efficiency of oocyte formation is enhanced.

INDUSTRIAL APPLICABILITY

According to the method for inducing immature oocytes of the embodiment, it is possible to induce immature oocytes from cells having an ability to differentiate into oocytes, such as pluripotent stem cells, easily by culturing them for a shorter period than a conventional method. According to the method for producing mature oocytes of the above embodiment, it is possible to produce mature oocytes from cells having an ability to differentiate into oocytes, such as pluripotent stem cells, easily in a large amount by culturing for a shorter period than a conventional method.

The invention claimed is:

1. A method for making an immature oocyte, the method comprising:
- (a) introducing nucleic acid sequences encoding folliculogenesis-specific basic helix-loop-helix (FIGLA), newborn oogenesis homeobox (NOBOX), LIM homeobox 8 (LHX8), and TATA-box binding protein like 2 (TBPL2) into an isolated mammalian pluripotent or epiblast cell, and
- (b) culturing the cell obtained in step (a) in a pluripotent medium such that an immature oocyte is obtained.

2. The method for making an immature oocyte according to claim 1, wherein the nucleic acid sequences consist of nucleic acid sequences encoding FIGLA, NOBOX, HLX8, and TBPL2.

3. The method for making an immature oocyte according to claim 2, wherein the immature oocyte obtained in step (b) is in an aggregate comprising pluripotent cells and ovarian somatic cells.

4. The method for making an immature oocyte according to claim 1, further comprising introducing a nucleic acid sequence encoding signal transducer and activator of transcription 3 (STAT3) into the isolated mammalian pluripotent cell.

5. The method for making an immature oocyte according to claim 1, further comprising introducing a nucleic acid sequence encoding spermatogenesis and oogenesis specific basic helix-loop-helix 1 (SOHLH1), SUB1 regulator of transcription (SUB1), or dynein light chain 1 (DYNLL1) into the isolated mammalian pluripotent cell.

6. The method for making an immature oocyte according to claim 1, further comprising introducing a nucleic acid sequences encoding SOHLH1, SUB1, and DYNLL1 into the isolated mammalian pluripotent cell.

7. The method for making an immature oocyte according to claim 1, wherein the cell is a pluripotent cell.

8. A method for making a mature oocyte, the method comprising:
- (a) introducing nucleic acid sequences encoding folliculogenesis-specific basic helix-loop-helix (FIGLA), newborn oogenesis homeobox (NOBOX), LIM homeobox 8 (LHX8), and TATA-box binding protein like 2 (TBPL2) into an isolated mammalian pluripotent cell,
- (b) culturing the cell obtained in step (a) in a pluripotent medium such that an immature oocyte is obtained, and
- (c) culturing the immature oocyte obtained in step (b) in a medium comprising follicular stimulating hormone, epidermal growth factor (EGF), human chorionic gonadotropin (hGC), and serum such that a mature oocyte is obtained.

9. The method for making a mature oocyte according to claim 8, further comprising introducing a nucleic acid sequence encoding signal transducer and activator of transcription 3 (STAT3) into the isolated mammalian pluripotent cell.

* * * * *